(12) United States Patent
Steger

(10) Patent No.: US 8,382,085 B2
(45) Date of Patent: Feb. 26, 2013

(54) COMPUTER-CONTROLLED MACHINING CENTER WITH A CLAMPING DEVICE FOR DENTAL WORKPIECE MILLING

(76) Inventor: Heinrich Steger, Bruneck (IT)

( * ) Notice: Subject to any disclaimer, the term of this patent is extended or adjusted under 35 U.S.C. 154(b) by 4 days.

(21) Appl. No.: 12/856,804

(22) Filed: Aug. 16, 2010

(65) Prior Publication Data

US 2011/0018184 A1 Jan. 27, 2011

Related U.S. Application Data

(63) Continuation of application No. PCT/EP2009/000858, filed on Feb. 6, 2009.

(30) Foreign Application Priority Data

Feb. 15, 2008 (AT) .................................. A 252/2008

(51) Int. Cl.
*B23Q 1/64* (2006.01)
(52) U.S. Cl. .............................. 269/57; 409/219; 433/49
(58) Field of Classification Search ............ 269/57; 248/278.1; 433/49; 409/219; *B23Q 11/00*
See application file for complete search history.

(56) References Cited

U.S. PATENT DOCUMENTS

| | | | | |
|---|---|---|---|---|
| 3,382,740 | A * | 5/1968 | Lotta ................................... | 408/3 |
| 4,426,763 | A * | 1/1984 | Hornok et al. ..................... | 483/6 |
| 5,524,510 | A * | 6/1996 | Davies et al. ................. | 76/108.2 |
| 5,885,199 | A * | 3/1999 | Shao ................................. | 483/19 |
| 6,682,276 | B2 | 1/2004 | Harami et al. | |
| 2004/0072121 | A1 | 4/2004 | Filser et al. | |
| 2006/0188352 | A1 | 8/2006 | Krosta et al. | |

FOREIGN PATENT DOCUMENTS

| | | |
|---|---|---|
| DE | 20 2006 015 334 U1 | 12/2006 |
| DE | 10 2006 027 395 A1 | 12/2007 |
| DE | 10 2006 027 397 A1 | 12/2007 |
| EP | 1 201 351 A2 | 5/2002 |
| EP | 1695791 A1 | 8/2006 |
| GB | 2 293 994 A | 4/1996 |
| WO | 02/45614 A1 | 6/2002 |
| WO | 2007/003355 A1 | 1/2007 |
| WO | 2007/143764 A2 | 12/2007 |
| WO | 2007/143765 A1 | 12/2007 |

OTHER PUBLICATIONS

International Search Report of PCT/EP2009/000858, Dated Apr. 14, 2010.
Austrian Patent Office Search Report of A 252/2008, Dated Nov. 20, 2008.

\* cited by examiner

*Primary Examiner* — Lee D Wilson
*Assistant Examiner* — Jamal Daniel
(74) *Attorney, Agent, or Firm* — Laurence A. Greenberg; Werner H. Stemer; Ralph E. Locher

(57) ABSTRACT

A computer-controlled machining center, particularly a CAD/CAM cutting device for dental technology applications, includes a clamping device with a displaceably supported holding device on which a carrier plate for receiving a molded blank is supported. The carrier plate is formed with at least one passage opening to accommodate the molded blank pivotally about a pivot axis (a) that is substantially parallel to the main plane of the carrier plate. A clamping assembly allows the shaping blank to be mounted in the through opening rotatably about an axis of rotation (b) that extends parallel to the main plane of the carrier plate and encloses a given angle, preferably 90°, with the pivot axis (a) of the carrier plate.

21 Claims, 4 Drawing Sheets

COMPUTER-CONTROLLED MACHINING CENTER WITH A CLAMPING DEVICE FOR DENTAL WORKPIECE MILLING

CROSS-REFERENCE TO RELATED APPLICATION

This application is a continuation, under 35 U.S.C. §120, of copending international application No. PCT/EP2009/000858, filed Feb. 6, 2009, which designated the United States; this application also claims the priority, under 35 U.S.C. §119, of Austrian patent application No. A 252/2008, filed Feb. 15, 2008; the prior applications are herewith incorporated by reference in their entirety.

BACKGROUND OF THE INVENTION

Field of the Invention

The invention pertains to a clamping device for a computer-controlled, chip-removing processing machine, in particular for a CAD/CAM milling device for the production of dental-technology workpieces having a displaceably mounted holding device on which a carrier plate for receiving a shaping blank is supported.

In a known CAD/CAM system for the production of dental-technology workpieces firstly a model of the tooth stump is three-dimensionally measured and the structure of the workpiece to be produced is calculated under computer control. On the basis of those data a milling program for a milling machine is calculated, which mills the desired structure out of a shaping blank. In that case the shaping blank comprises presintered zirconium oxide which is substantially softer in comparison with fully sintered material. The dental-technology workpiece produced in that way is then subjected to final sintering.

Prior art cutting machines for milling ceramic workpieces are based on conventional three-axis milling machines and are therefore only limitedly suitable for demanding free-form surface machining as is required in relation to dental-technology workpieces. Thus in the known milling systems the workpiece has to be changed in respect of its clamping, inter alia, for machining the second side, which can obviously result in inaccuracies.

SUMMARY OF THE INVENTION

It is accordingly an object of the invention to provide a computer-controlled cutting machine which overcomes various disadvantages of the heretofore-known devices and methods of this general type and which provides for a computer-controlled cutting machine of the kind set forth above that enables a precise manufacture of dental-technology workpieces, while at the same time providing for a simple operation and also representing an inexpensive solution.

With the foregoing and other objects in view there is provided, in accordance with the invention, a CAD/CAM milling device for processing dental-technology workpieces, the device comprising:

a clamping device for a shaping blank, the clamping device having a displaceably mounted holding device and a carrier plate pivotally mounted to the holding device about an axis of rotation substantially parallel to a main plane of the carrier plate;

the carrier plate having at least one through opening formed therein for receiving the shaping blank; and a clamping assembly for rotatably mounting the shaping blank in the at least one through opening about an axis of rotation extending substantially parallel to the main plane of the carrier plate and enclosing a given angle with the axis of rotation of the carrier plate.

In other words, the carrier plate has at least one through opening in which the shaping blank is or can be arranged pivotally at least about an axis of rotation that is substantially parallel to the main plane of the carrier plate. In addition, the shaping blank can be rotated about an axis of rotation that is also substantially parallel to the main plane of the carrier plate and which encloses an preferred angle of 90° with the first pivot axis.

The device provides that two of the necessary five axes of movement for free-form surface machining are permitted by way of the rotatability and pivotability of the shaping blank.

A preferred embodiment of the invention provides that the carrier plate is supported at the displaceably supported holding device rotatably about an axis of rotation that is substantially parallel to the main plane thereof, wherein the axis of rotation of the shaping blank arranged pivotally in the at least one through opening includes an angle of preferably 90° with the axis of rotation of the carrier plate. That affords a particularly stable solution, wherein the carrier plate can be placed in position in a simple fashion by way of a drive motor acting directly on the mounting of the carrier plate.

A simple and also stress-free possible way of fixing the shaping blank in the through opening is afforded if—as a further embodiment provides—the shaping blank is or can be arranged in the at least one through opening by means of a substantially disc-shaped holding element, wherein the shaping blank is fixed in a simple and secure fashion if the shaping blank is arranged, preferably glued, in a through opening in the disc-shaped holding element.

In accordance with a further preferred embodiment of the invention the pivotable arrangement of the shaping blank in the at least one through opening is effected by means of a clamping assembly for fixing the shaping blank, wherein the clamping assembly is arranged on the carrier plate pivotally at least about an axis of rotation that is parallel to the main plane of the carrier plate, wherein a secure hold for the shaping blank can be ensured if the clamping assembly is of a substantially annular configuration, at least partially embracing the shaping blank, and the shaping blank is or can be arranged in the clamping assembly by means of the disc-shaped holding element.

A simple possible way of fixing the shaping blank arranged in the disc-shaped holding element is achieved if the clamping assembly has at least one gripping device for releasably fixing the holding element, in which respect it has proven to be advantageous for ease of handling if at least one gripping device has a gripping jaw which can be fixed preferably by means of a setting screw.

In other words, fixing of the shaping blank is effected by means of a disc-shaped holding element in the through opening of a carrier plate which is in two parts, wherein the two preferably annular parts of the carrier plate are arranged coaxially and are pivotable about two axes of rotation which are substantially normal to each other.

In accordance with a particularly preferred embodiment of the invention it is provided in that respect that the carrier plate is mounted to the holding device pivotally about an axis of rotation substantially parallel to its main plane and has precisely one preferably circular through opening in which there is pivotally supported an annular clamping assembly for fixing the shaping blank by means of a disc-shaped holding element, pivotally about an axis of rotation which includes a substantially right angle with the axis of rotation of the carrier plate and extends substantially parallel to the main plane of the carrier plate.

In a further embodiment of the invention the clamping device is of a compact structure if the displaceably mounted holding device is of a hooped-shaped configuration, preferably being substantially U-shaped, and has two substantially parallel limbs and a leg connecting the two limbs, wherein the carrier plate is mounted rotatably between the lateral limbs of the hoop-shaped holding device.

In that respect a particularly low structural height can be achieved if the maximum spacing of the axis of rotation of the carrier plate relative to the leg of the hoop-shaped holding device is less than the maximum spacing from the axis of rotation to the outer edge of the carrier plate so that the hoop-shaped holding device limits the angle of rotation of the carrier plate or serves as an abutment for the latter.

In that respect machining of the shaping blank on all sides can also be achieved even if the angle of rotation for the carrier plate is less than 150°, in which respect a low structural height in respect of the clamping device and at the same time machining of the shaping blank on all sides is ensured if the angle of rotation for the carrier plate is about 100°.

The invention further provides that the shaping blank is supported in the at least one through opening rotatably about at least one axis of rotation over an angle of greater than 270°, in which respect it has proven to be advantageous if the shaping blank is rotatable over an angle around 360°.

In other words to be able to machine the shaping blank from all sides and to implement complicated three-dimensional shapes in that way it is sufficient if the shaping blank is rotatable or pivotable in one direction through 360° and is mounted pivotally normal thereto through an angle of rotation of about 100°.

The CAD/CAM milling device for the production of dental-technology workpieces is implemented relatively simple because, due to the displaceable mounting of the holding device and the two axes of pivot movement which are afforded by way of the shaping blank mounting according to the invention, the mounting for the machining tool only has to be able to implement two axes of movement.

In order to avoid the machining tool having to be changed between various machining operations, in a further embodiment of the invention there is provided a positioning device for at least two machining tools arranged in substantially parallel mutually juxtaposed relationship, wherein the machining tools are mounted displaceably in such a way that in each case precisely one machining tool is movable into the working position—with respect to the clamping device.

That displaceable mounting of the machining tools therefore ensures the fourth axis of movement while the fifth axis of movement is afforded in accordance with a further embodiment of the invention insofar as at least one and preferably a plurality of machining tools is or are mounted to the positioning device displaceably in a first direction of movement and the positioning device has an actuating element for moving one of the machining tools in a second direction of movement substantially normal to the first direction of movement, or by virtue of the fact that the positioning device has an actuating element for each machining tool.

In that respect a structurally simple solution is afforded if the actuating element has a piston-cylinder unit, a preferred embodiment of the invention providing that the actuating element acts pneumatically. It will be appreciated that hydraulically acting actuating elements are also suitable for embodying the idea of the invention.

Other features which are considered as characteristic for the invention are set forth in the appended claims.

Although the invention is illustrated and described herein as embodied in a clamping device for a computer-controlled machining center, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
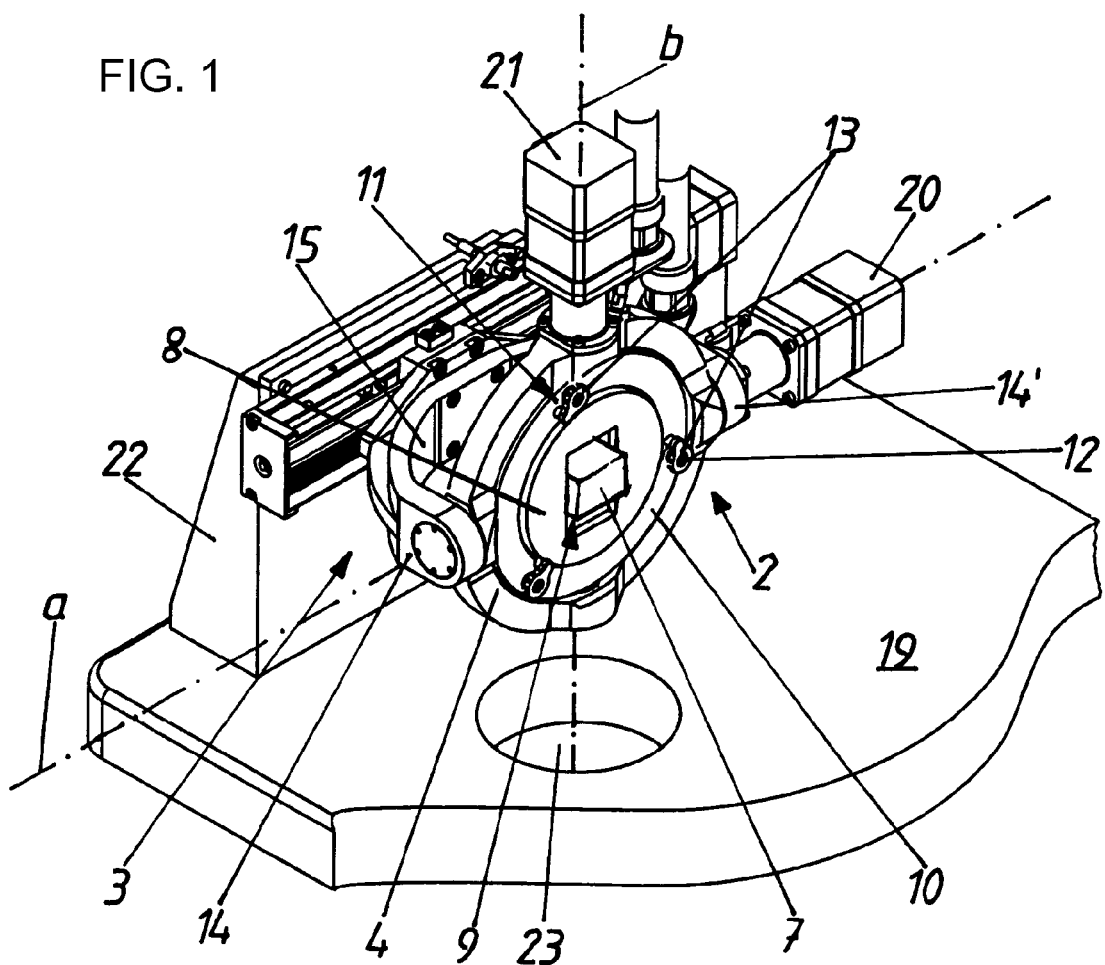
FIG. 1 is a perspective view of a first embodiment of a clamping device according to the invention.

Referring now to the figures of the drawing in detail and first, particularly, to FIG. 1 thereof, there is shown a perspective view of a first embodiment of a clamping device 2 according to the invention. The clamping device 2 is disposed on a base 22 displaceably by way of the hoop-shaped holding device 3. The base 22 is disposed on a base plate 19 of a computer-controlled, cutting machine 1, in such a way that the dust passage opening 23 in the base plate 19 is disposed directly beneath the shaping blank 7 to be machined.

The shaping blank 7 is fixed, for example glued, in a through opening 9 of a disc-shaped holding element 8 and is fixed in the clamping assembly 10 by means of the disc-shaped holding element 8. For that purpose the clamping assembly 10 has a plurality of gripping devices 11. Each of the gripping devices 11 includes a gripping jaw 13 which is arrested by way of a setting screw 12 so that the disc-shaped holding element 8 with the shaping blank 7 fixed therein can be fixed in position.

Figure 2A:
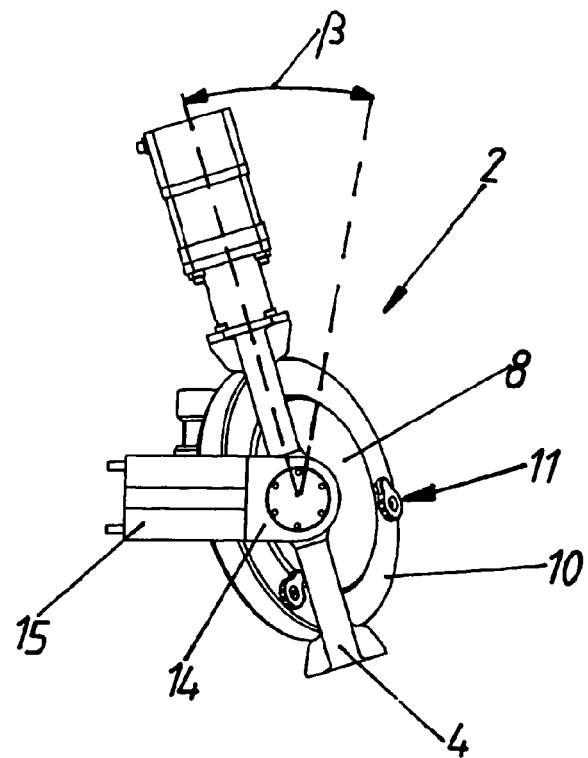
FIGS. 2A-2B show embodiments with the pivoted clamping device.
Figure 2B:
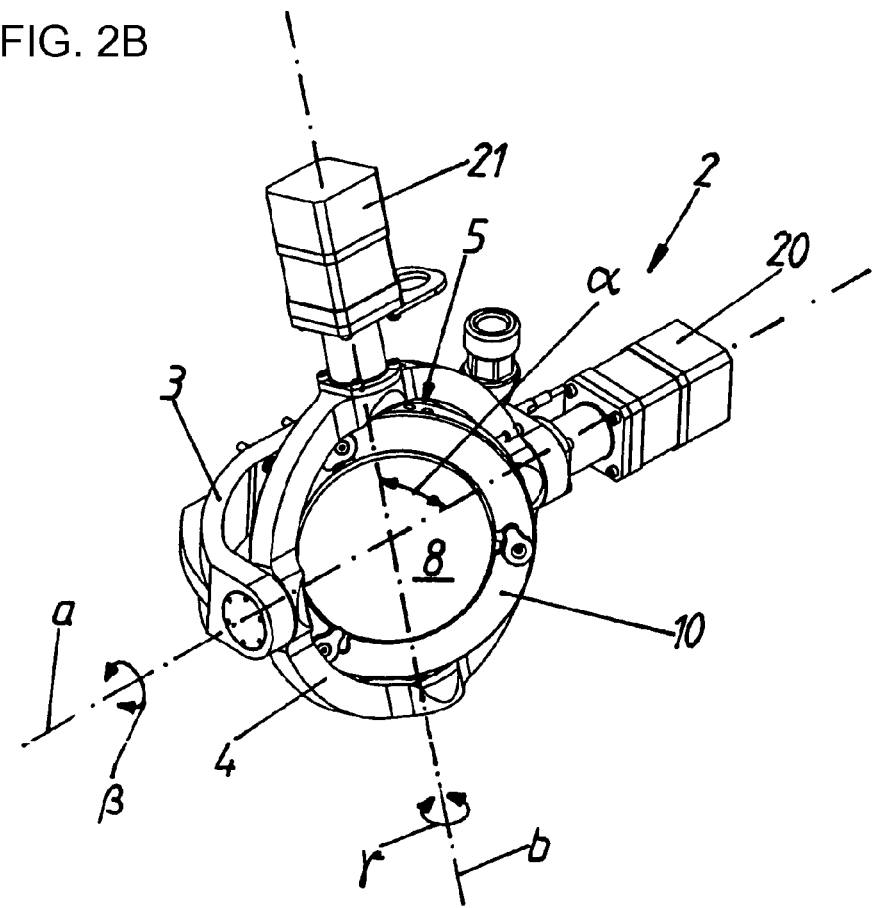

Referring now more particularly to FIGS. 2A and 2B, the carrier plate 4 of the clamping device 2 is rotatably or pivotally mounted to the holding device 3 about an axis of rotation a. A spacing distance from the axis of rotation a to the leg 15 is smaller than a spacing distance from the axis of rotation a to an outer edge of the carrier plate 4. A pivot angle or angle of rotation β of the carrier plate 4 is limited by the leg 15 of the holding device 3.

The clamping assembly 10 which is also of an annular configuration is rotatably mounted in the through opening 5 of the annular carrier plate 4 about an axis of rotation b. The latter encloses a right angle α with the axis of rotation a, and the clamping assembly 10 is rotatable about the axis b through an angle of rotation γ of 360°.

In other words the carrier plate is formed by two coaxial rings of which the outer ring is rotatably (pivotally) mounted to the holding device and the inner ring is rotatably mounted to the outer ring, and the axes of rotation of the outer and inner rings are perpendicular and enclose an angle of 90°.

The pivotal or rotary movement of the carrier plate 4 about the axis of rotation a and the clamping mechanism 10 about the axis of rotation b is effected under computer control in the illustrated embodiment by way of drive units 20, 21.

Figure 3A:
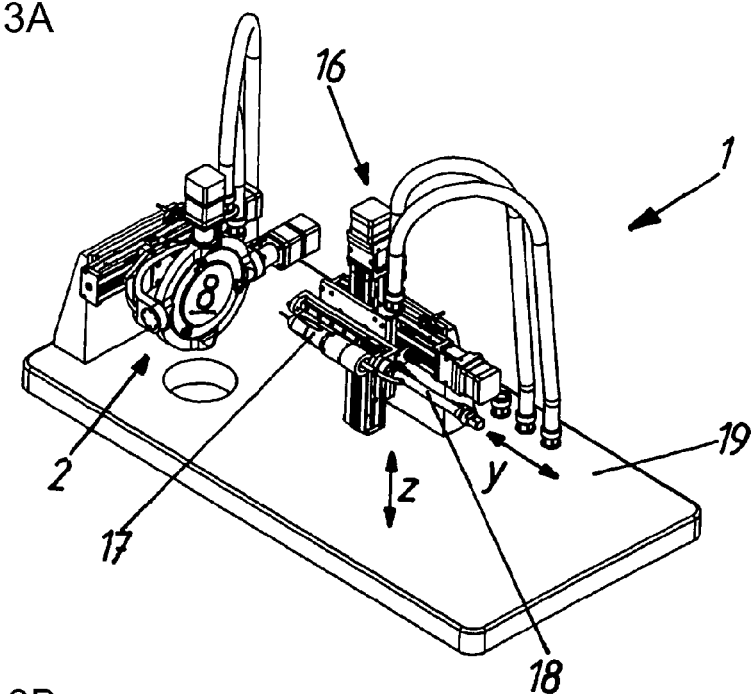
FIG. 3A is a perspective view of an embodiment of a cutting machine according to the invention.
Figure 3B:
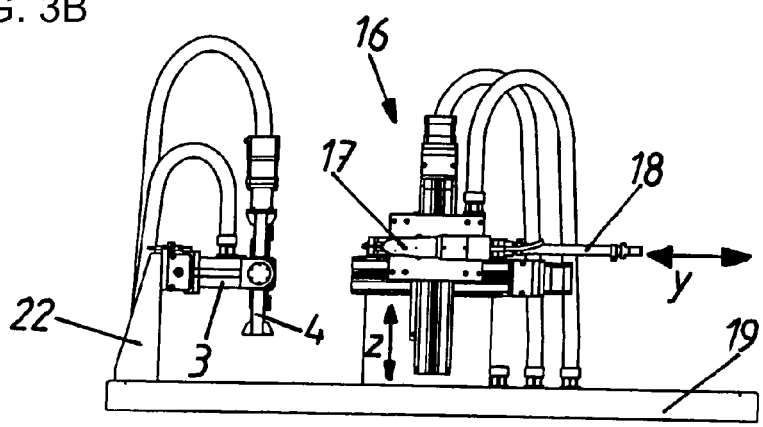
FIG. 3B is a front view thereof.
Figure 3C:
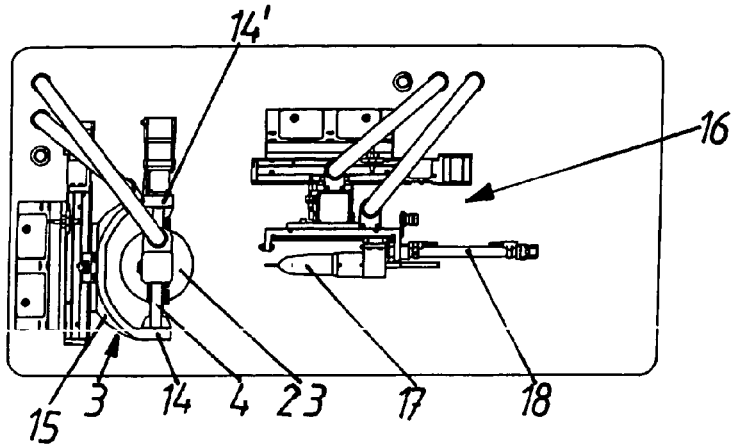
FIG. 3C is a plan view thereof.

FIGS. 3A to 3C illustrate an embodiment of a CAD/CAM milling device 1 according to the invention which has a clamping device 2 according to the invention. A positioning device 16 for a machining tool 17 is mounted to the base plate 19 horizontally spaced from the clamping device 2. The machining tool 17 is mounted displaceably in a first direction of movement z on the positioning device 16 and, after it has been moved into the appropriate vertical position, is moved in the direction of movement y in the direction of the clamping device 2 and away from same respectively by means of an actuating element 18 which in the illustrated embodiment is formed by a pneumatic piston-cylinder unit.

Figure 4:
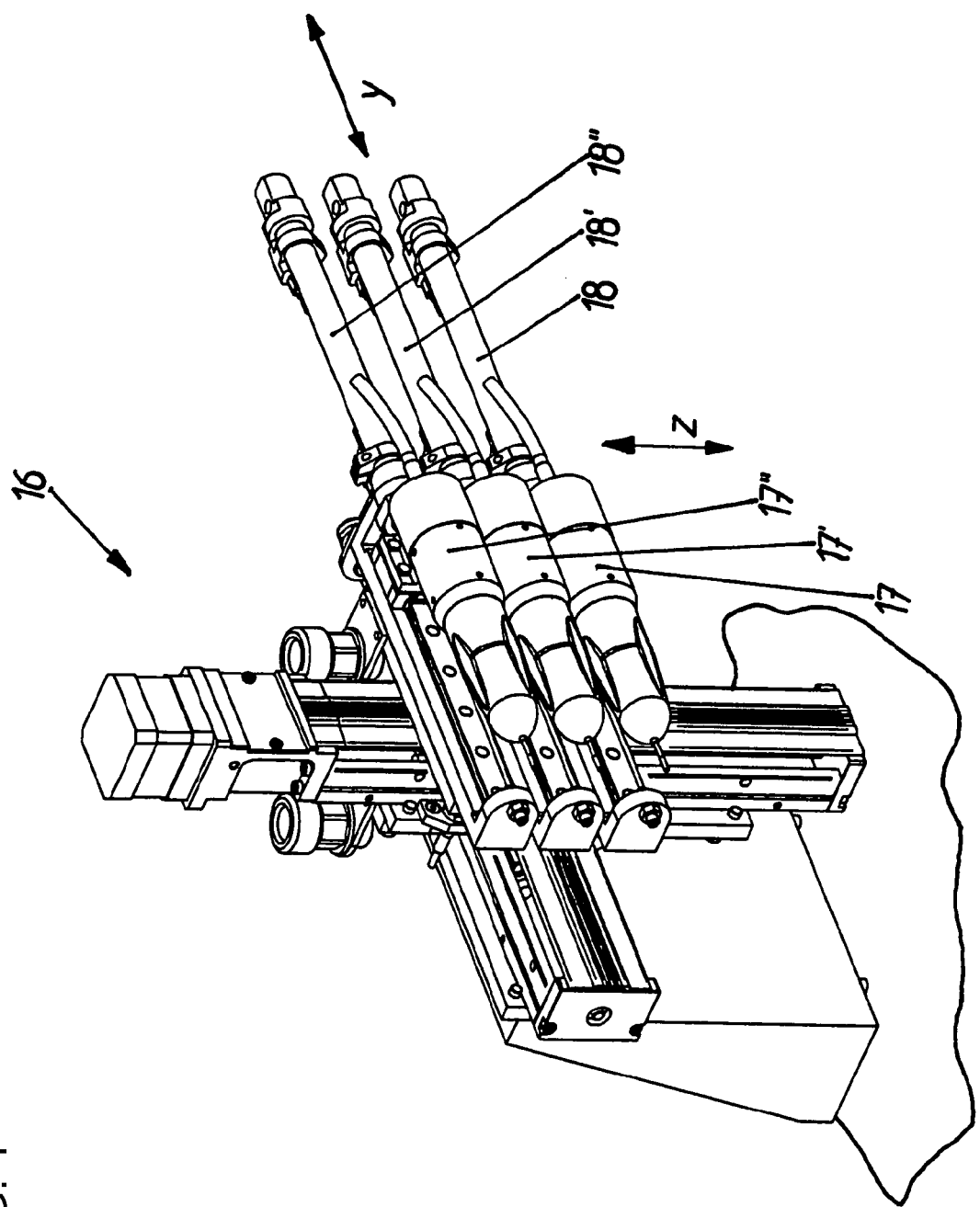
FIG. 4 is a perspective view of an embodiment of a positioning device according to the invention.

FIG. 4 shows a preferred embodiment of a positioning device 16 according to the invention. There, three machining tools 17, 17', 17" are arranged jointly displaceably in the direction of movement z on the positioning device 16. The positioning device 16 has an actuating element 18, 18', 18" in the form of a pneumatic piston-cylinder unit for each of the machining tools 17, 17', 17". That configuration affords the advantage that even when performing different milling or machining operations the machining tool 17, 17', 17" does not have to be changed as was hitherto usual, but the respectively required machining tool 17, 17', 17" is simply moved into the working position by displacement in the y and z directions.

It will be appreciated that the illustrated embodiments of clamping devices and the illustrated milling device are not to be interpreted in a restrictive sense but are only individual examples of numerous possible ways of embodying the concept of the invention of a clamping device having a rotatably mounted carrier plate, in the through opening of which a shaping blank can be rotatably supported.

The invention claimed is:

1. A CAD/CAM milling device for processing dental-technology workpieces, the device comprising:
    a computer-controlled cutting machine for cutting a shaping blank;
    a clamping device for the shaping blank, said clamping device having a displaceably mounted holding device and a carrier plate pivotally mounted to said holding device about an axis of rotation substantially parallel to a main plane of said carrier plate, said displaceably mounted holding device being a hoop-shaped device with two substantially parallel, lateral limbs and a leg connecting said limbs;
    said carrier plate being rotatably mounted between said lateral limbs and having at least one through opening formed therein for receiving the shaping blank; and
    a clamping assembly for rotatably mounting the shaping blank in said at least one through opening about an axis of rotation extending substantially parallel to the main plane of said carrier plate and enclosing a given angle with the axis of rotation of said carrier plate.

2. The milling device according to claim 1, wherein said clamping assembly is substantially annular and configured to surround the shaping blank at least partially when the shaping blank is disposed in said through opening.

3. The milling device according to claim 2, wherein said clamping assembly includes at least one gripping device for releasably fixing said holding device.

4. The milling device according to claim 3, wherein said at least one gripping device includes a gripping jaw.

5. The milling device according to claim 4, which comprises a setting screw disposed to secure said at least one gripping device.

6. The milling device according to claim 1, wherein, when the shaping blank is disposed in said through opening, the shaping blank is glued into the through opening of said holding element.

7. The milling device according to claim 1, wherein said clamping assembly is configured to rotatably mount the shaping blank in said at least one through opening about an angle of rotation greater than 270°.

8. The milling device according to claim 7, wherein the shaping blank is rotatable about an angle of 360°.

9. The milling device according to claim 1, wherein the given angle enclosed between the axis of rotation of said carrier plate and the axis of rotation of said clamping assembly is 90°.

10. The milling device according to claim 1, wherein an assembly comprising said carrier plate and said clamping assembly is formed by two coaxial rings, wherein an outer ring forms said carrier plate and is rotatably mounted to said holding device about the axis of rotation and an inner ring forms said clamping assembly and is mounted to said outer ring about the axis of rotation, and wherein the axes of rotation of said outer and inner rings enclose an angle of 90°.

11. The milling device according to claim 1, wherein said hoop-shaped device has a substantially U-shaped configuration.

12. The CAD/CAM milling device according to claim 1, further comprising:
    a positioning device for at least two machining tools disposed in substantially parallel mutually juxtaposed relationship, said machining tools being displaceably mounted such that in each case precisely one machining tool can be moved into a working position with respect to said clamping device holding a workpiece to be processed.

13. The milling device according to claim 12, wherein at least one machining tool is mounted to said positioning device displaceably in a first direction of movement and said positioning device has an actuating element for moving one of the machining tools in a second direction of movement substantially perpendicular to the first direction of movement.

14. The milling device according to claim 12, wherein said positioning device comprises an actuating element for each machining tool.

15. The milling device according to claim 14, wherein said actuating element comprises a piston-cylinder unit.

16. The milling device according to claim 14, wherein said actuating element is a pneumatically acting element.

17. A CAD/CAM milling device for processing dental-technology workpieces, the device comprising:
    a computer-controlled cutting machine for cutting a shaping blank;
    a clamping device for the shaping blank, said clamping device having a displaceably mounted holding device and a carrier plate pivotally mounted to said holding device about an axis of rotation substantially parallel to a main plane of said carrier plate;
    said carrier plate having at least one through opening formed therein for receiving the shaping blank;
    a clamping assembly for rotatably mounting the shaping blank in said at least one through opening about an axis of rotation extending substantially parallel to the main plane of said carrier plate and enclosing a given angle with the axis of rotation of said carrier plate; and a substantially disc-shaped holding element configured to enable the shaping blank to be arranged in said clamping assembly, said disc-shaped holding element having a through opening formed therein for receiving and holding the shaping blank.

18. A CAD/CAM milling device for processing dental-technology workpieces, the device comprising:

a clamping device for a shaping blank, said clamping device having a displaceably mounted holding device and a carrier plate pivotally mounted to said holding device about an axis of rotation substantially parallel to a main plane of said carrier plate;

said carrier plate having at least one through opening formed therein for receiving the shaping blank;

and wherein said displaceably mounted holding device is a hoop-shaped device with two substantially parallel, lateral limbs and a leg connecting said limbs, and wherein said carrier plate is rotatably mounted between said lateral limbs, and a clamping assembly for rotatably mounting the shaping blank in said at least one through opening of said carrier plate about an axis of rotation extending substantially parallel to the main plane of said carrier plate and enclosing a given angle with the axis of rotation of said carrier plate;

and a first drive unit provided on said holding device to effect rotation of said carrier plate;

and a second drive unit provided on said carrier plate to effect rotation of said clamping assembly.

19. The CAD/CAM milling device according to claim 8, which further comprises a substantially disc-shaped holding element configured to enable the shaping blank to be arranged in said clamping assembly, said disc-shaped holding element having a through opening formed therein for receiving and holding the shaping blank.

20. The CAD/CAM milling device according to claim 18, wherein an assembly comprising said carrier plate and said clamping assembly is formed by two coaxial rings, wherein an outer ring forms said carrier plate and is rotatably mounted to said holding device about the axis of rotation and an inner ring forms said clamping assembly and is mounted to said outer ring about the axis of rotation, and wherein the axes of rotation of said outer and inner rings enclose an angle of 90°.

21. The CAD/CAM milling device according to claim 18, comprising a computer-controlled cutting machine for cutting the shaping blank.

* * * * *